United States Patent
Caseault et al.

(10) Patent No.: US 7,289,601 B2
(45) Date of Patent: Oct. 30, 2007

(54) DIGITAL IMAGE COLLECTOR FOR X-RAY SYSTEMS

(75) Inventors: Jean Caseault, Beauport (CA); Min Wang, Ste-Foy (CA); Simon Thibault, Ste-Foy (CA)

(73) Assignee: Imascope Inc., Gatineau, Quebec (CA)

( * ) Notice: Subject to any disclaimer, the term of this patent is extended or adjusted under 35 U.S.C. 154(b) by 95 days.

(21) Appl. No.: 11/000,533

(22) Filed: Dec. 1, 2004

(65) Prior Publication Data
US 2005/0151085 A1 Jul. 14, 2005

(51) Int. Cl.
*H05G 1/64* (2006.01)
(52) U.S. Cl. ..................... 378/98.3; 250/368
(58) Field of Classification Search ............... 250/583, 250/586, 587, 368; 378/98.3, 62
See application file for complete search history.

(56) References Cited

U.S. PATENT DOCUMENTS

| | | | |
|---|---|---|---|
| 4,379,348 A * | 4/1983 | Haas et al. ................. | 378/57 |
| 4,736,397 A | 4/1988 | Velasquez | |
| 5,138,642 A | 8/1992 | McCroskey et al. | |
| 5,187,730 A * | 2/1993 | Fujihara ..................... | 378/97 |
| 5,493,600 A | 2/1996 | Jacobson | |
| 5,585,638 A | 12/1996 | Hoffman | |
| 5,712,890 A | 1/1998 | Spivey et al. | |
| 5,723,865 A | 3/1998 | Trissel et al. | |
| 5,790,629 A * | 8/1998 | Svensson et al. .......... | 378/98.7 |
| 5,872,595 A | 2/1999 | Monahan | |
| 6,047,042 A | 4/2000 | Khutoryansky et al. | |
| 6,192,105 B1 | 2/2001 | Hunter et al. | |
| 6,298,109 B1 | 10/2001 | Ergun et al. | |
| 6,353,657 B1 | 3/2002 | Bayrock et al. | |
| 6,385,289 B1 | 5/2002 | Kikuchi | |
| 6,459,765 B1 | 10/2002 | Ganin et al. | |

(Continued)

FOREIGN PATENT DOCUMENTS

JP 2000183516 A * 6/2000

(Continued)

OTHER PUBLICATIONS

Melles Griot "The Practical Application of Light" 1999, pp. 13.26, 13.27, 13.39.*
Melles Griot (1999) "The Practical Application of Light" pp. 13.26, 13.27, 13.29.*

*Primary Examiner*—Courtney Thomas
(74) *Attorney, Agent, or Firm*—Shin Hung; Borden Ladner Gervais LLP (57) ABSTRACT

A digital X-ray system for capturing high quality images by maximizing the collection of emitted light from an intensifying screen in response to X-ray impact. The digital X-ray system includes a housing having a fluorescent intensifying screen for receiving emitted X-rays, two reflectors for maximizing light collection and optimizing the light path from the intensifying screen, and a lens assembly. A CCD chip receives the light from the lens assembly, to provide a digital image for immediate on-board processing or post-processing by a computer. The housing is compact, and can be used as a direct replacement for traditional film cartridges without major modifications to the system. The lens assembly includes freeform matched lenses to remove optical distortions, and the housing includes a light sensor for providing exposure measurement and feedback. The system is designed to be quasi-monochromatic to maintain consistent image quality over the entire area of the intensifying screen.

23 Claims, 7 Drawing Sheets

U.S. PATENT DOCUMENTS

| | | |
|---|---|---|
| 6,546,076 B1 | 4/2003 | Hull et al. |
| 6,717,174 B2 | 4/2004 | Karellas |
| 6,778,216 B1 * | 8/2004 | Lin ........................ 348/333.11 |
| 2003/0142784 A1 | 7/2003 | Suzuki et al. |
| 2004/0165095 A1 * | 8/2004 | Shimizu et al. ............. 348/335 |

FOREIGN PATENT DOCUMENTS

| | | |
|---|---|---|
| WO | WO 9617265 A1 * | 6/1996 |
| WO | WO9617265 A1 * | 6/1996 |

* cited by examiner

DIGITAL IMAGE COLLECTOR FOR X-RAY SYSTEMS

FIELD OF THE INVENTION

The present invention relates generally to digital X-Ray systems. In particular, the present invention relates to light collection apparatus for digital X-Ray systems.

BACKGROUND OF THE INVENTION

X-ray systems are commonly used in medical applications to provide intrusive-free visual assessment of tissues and bones. Such systems are commonly found in hospitals, clinics and even veterinarian clinics to assist doctors in diagnosing problems with their patients.

Conventional X-ray systems use films exposed to an intensifying screen (also known as a phosphorous screen or fluorescent screen). This screen converts the high-energy photons (X-rays) that reach the screen into lower energy photons (typically visible light), which then imprints the object being exposed onto a film. The film is then developed and subsequently viewable with a suitable backlighting source, such as a light table for example. This process is well known and has been refined for over a century, and is capable of providing high-resolution images.

Figure 1:
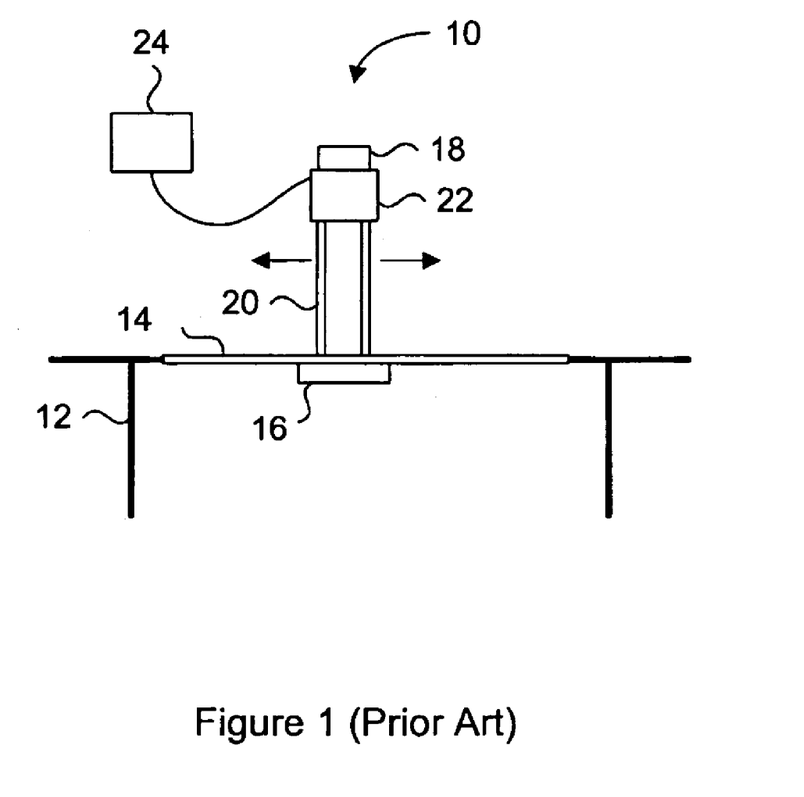
FIG. 1 shows a conventional table X-ray system of the prior art.

A conventional table X-ray system is shown in FIG. 1. This particular type of x-ray system is commonly used in veterinarian clinics. X-ray system 10 includes a table 12 with a working surface 14 made of bakelite or formica. Mounted on the underside of the working surface 14 is a detachable film cartridge/cassette 16, which is physically connected to an x-ray emitter 18 via support arms 20. The film cartridge/cassette 16 includes an intensifying screen in proximity to the underside of the working surface 14, and film underneath the screen for capturing the photons emitted from the intensifying screen. The x-ray emitter 18 is fitted with an x-ray tube 22 and a collimator to help confine emitted x-rays to the area of interest. The x-ray emitter 18 and film cartridge/cassette 16 are configured such that x-rays from x-ray emitter 18 will always reach the film cartridge/cassette 16. In the presently shown example, film cartridge/cassette 16, x-ray emitter 18 and support arms 20 are slidable along the working surface 14 as a unit in the directions indicated by the arrows in FIG. 1. This allows the operator to position the emitter/cartridge assembly as desired. A generator 24 typically mounted to a nearby wall or under the table 12 supplies power to x-ray emitter 18. An alternate configuration has the intensifying screen mounted vertically, with the emitter/cartridge assembly slidable in the vertical axis, which is more suitable for chiropractors, for example. Those of skill in the art will understand that working surface 14 can be made of any suitable material that facilitates the transmission of X-rays to the intensifying screen of the cartridge/cassette 16.

Figure 2:
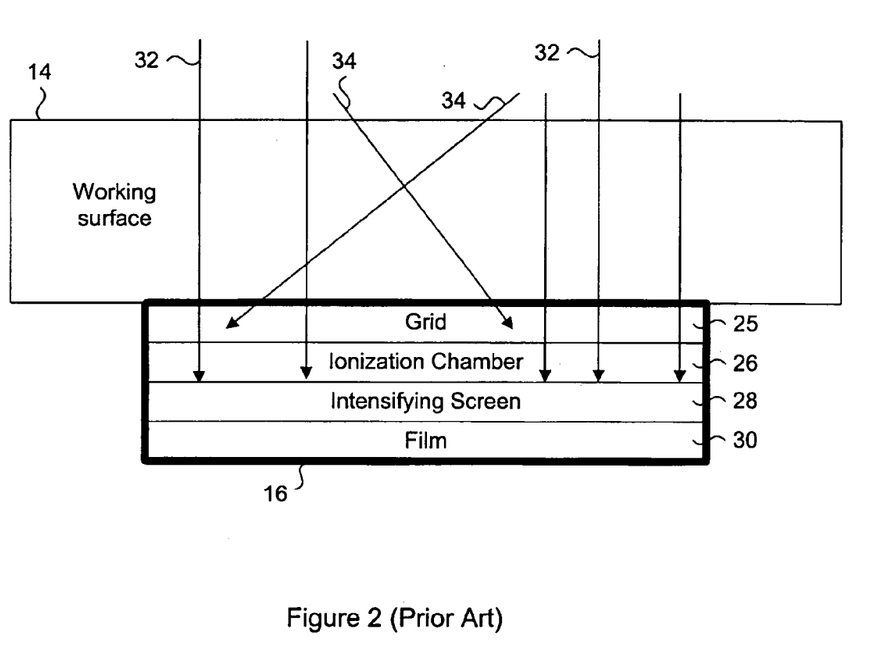
FIG. 2 is an illustration of a film cartridge used in the conventional system shown in FIG. 1.

FIG. 2 shows further details of the cartridge/cassette 16 shown in FIG. 1, and in particular, the layered composition of the cartridge/cassette 16. As previously shown, cartridge/cassette 16 is positioned underneath working surface 14 of the table 12. The area of cartridge/cassette 16 is approximately 14×17 inches, with a thickness that is determined by the thickness of the individual layer components. The cartridge/cassette 16 generally includes an optional X-ray grid 25, an auto ionization chamber 26, an intensifying screen 28, and film 30. As illustrated in FIG. 2, X-rays 32 pass through an object (not shown) placed on top of the working surface 14, through the X-ray grid 25 and ionization chamber 26. The X-rays colliding with the intensifying screen 28 cause light to be emitted towards the film 30 for image capture. X-ray grid 25 functions as a filter to prevent scattered X-rays 34 deflected from the object from passing through to the intensifying screen 28, as these scattered X-rays contribute to image noise, and are hence undesirable. Ionization chamber 26 is a device that intercepts a portion of the X-rays and sends a signal to the operator when a predetermined dose has been reached. The ionization chamber 26 includes collection zones of a predetermined area that would be positioned beneath vital organs of a patient, such as lungs, to ensure that sufficient X-rays are received to obtain a satisfactory image. Unfortunately, the ionization chamber 26 effectively blocks some of the X-rays 32 from reaching the intensifying screen 28, thus requiring an increase in the emitted dose to compensate for the absorption by the ionization chamber 26. Thus, the loss of X-rays reduces the efficiency of the system.

In operation, the operator places the specimen upon the table and positions the emitter/cartridge assembly. Activation of the x-ray emitter 18 at a particular energy level (kV), current (mA), and time in seconds (s), determines the delivered dose. Once the desired dose has been delivered, the film cartridge/cassette 16 is detached from the assembly and developed in a dark room.

The disadvantages of film-based x-ray systems include film cost, chemical developer cost, exclusive use of a room as a dark room (or the purchase of an automatic film processor), and single master copy of the image. Of course, this leads to further disadvantages such as storage for the film and chemicals, proper disposal for used film and chemicals, and careful packaging and mailing of the single image copy to other experts when further assessment is required.

Naturally, with the advent of digital imaging technology and charge coupled device (CCD) technology, filmless X-ray systems have been developed to directly take X-ray images and display them on a computer screen for immediate evaluation. Although the digital imaging process is significantly faster and solves many of the disadvantages inherent with film based systems, presently available digital filmless x-ray systems provide image quality inferior to those of film-based x-ray systems or high-quality systems at a prohibitive cost for private clinics.

A critical factor to image quality in digital x-ray systems is the ability of the CCD sensor to collect sufficient light emitted by the intensifying screen. X-ray films are positioned directly underneath the intensifying screen, and thus maximize emitted light collection. A digital sensor on the other hand, must use an optical element that redirects the light from the intensifying screen onto the CCD. In order to collect the complete image from the 14×17 inch intensifying screen, the CCD must be a certain distance apart from the screen. The distance is significant due to the large viewing angle of the optical design which redirects a 14×17 surface to the tiny surface of the CCD. Consequently, in most optical designs, only a small portion of the light is collected. For example, only about 2% of the light emitted from the intensifying screen will reach the CCD.

In addition the electronic circuits of the CCD and those coupled to the CCD can be damaged by X-rays that pass through the working surface. The CCD circuit assembly must therefore be positioned outside of the path of emitted X-rays and, depending on the positioning of the CCD circuit, redirection of the emitted photons is required.

This usually leads to increased size of the CCD sensor and associated optics assembly to facilitate the optical design and improve system performance, hence increased system costs and size. Ideally, the housing of the CCD sensor and its associated optics should be minimized so as not to overly limit the range of positioning of the X-ray emitter and CCD sensor assembly. For example, in the veterinary clinics, the X-ray assembly must be positionable anywhere along the working surface. In a chiropractor clinic, patients typically stand, therefore the X-ray assembly must be positionable anywhere vertically.

Many designs have been proposed to redirect the light path and increase the amount of light being collected. The most common technique includes combinations of spherical lenses that collect light over a large surface and concentrate the light beams onto one CCD chip. Unfortunately, to collect as much light as possible, it is imperative to position the lens assembly as close to the screen as possible, or use very large lenses. The resulting image distortions are significant and limit the usefulness of this technique. Furthermore, the lens design prevents the light from being evenly distributed, and more light is collected at the center of the screen than at the edges.

Another common technique is to use many CCDs. Since the area to cover per CCD is smaller, the lens elements can be put closer to the screen, thus collecting more light and increasing the overall system resolution. The resulting image is a combination of images generated by each CCD and merged/tiled together. In order to realign pictures, each CCD slightly overlaps its neighbouring CCD. However any distortion in the source images will increase the complexity of aligning the images together. Complex DSP programs and CCD alignment procedures are therefore required to minimize alignment problems, but undesired artifacts may be created. This, of course, has also the disadvantage of increasing the system cost.

Another limitation of prior art digital X-ray imaging systems is the inconsistent image quality over the intensifying screen. As the CCD is brought closer to the intensifying screen, thus increasing the viewing angle, image sharpness is lost since the light energy is dispersed over several pixels, especially at the edges of the image. Therefore, inconsistent quality across the image is obtained, even though relatively large amounts of light may be collected. This effect limits quality image capture to a smaller area of the intensifying screen.

It is, therefore, desirable to provide a digital filmless x-ray imaging system which can maximize collection of emitted light from an intensifying screen while minimizing distortions and other image degrading effects.

SUMMARY OF THE INVENTION

It is an object of the present invention to obviate or mitigate the disadvantages of previous digital x-ray systems. In particular, it is an object of the invention to maximize the collection of emitted light while reducing the size of the x-ray imaging system. It is a further object of the present invention to maximize the light path between the intensifying screen and the lens assembly while maintaining image quality of optical designs with similar applications.

In a first aspect, the present invention provides a digital image capturer for receiving X-rays and providing digital image data corresponding to the received X-rays. The digital image capturer includes a light generator for receiving the X-rays and for emitting light in response to the received X-rays, a first planar reflector for reflecting the emitted light, a second planar reflector positioned for receiving the emitted light from the first planar reflector, and reflecting the emitted light, and a fast relay-optics system for receiving the emitted light from the second planar reflector and for focusing the emitted light onto a digital imaging device, the digital imaging device generating the digital image data.

According to an embodiment of the first aspect, the light generator can include a light shield positioned for receiving the X-rays and for blocking external light, and an intensifying screen adjacent to the light shield for emitting light in response to the X-rays passing through the light shield. The light generator can include an X-ray grid mounted to the light shield, and the light shield can be constructed from a material opaque to light and transparent to X-rays. The material of the light shield can be selected from the group consisting of bakelite and carbon fiber.

According to another embodiment of the first aspect, the fast relay-optics system can include a CCD electronics board having the digital imaging device, and a lens assembly positioned for receiving the emitted light from the second planar reflector, the lens focusing the emitted light onto the digital imaging device. The digital imaging device can be either a CCD chip or a CMOS sensor, and the CCD electronics board can include a microprocessor, such as a digital signal processor, for receiving digital image data from the digital imaging device and for executing image processing algorithms upon the digital image data. The CCD electronics board can include non-volatile memory for storing imaging device calibration data, which can include at least one of pixel gain coefficients, pixel dark noise data, dead pixel mapping data and distortion data. The lens assembly can be quasi-monochromatic and include a combination of spherical and aspherical lenses. The lens assembly includes one lens coated with a 2-cavity bandpass filter made of $SiO_2$ and $ZrO_2$ to restrict light having wavelengths less than about 530 nm and greater than about 570 nm.

In yet other embodiments of the present aspect, the digital image capturer further includes at least one light sensor coupled to the digital imaging device, where the at least one light sensor includes a matched lens for receiving emitted light from a specific area of the intensifying screen. The first planar reflector and the second planar reflector can be housed in an imaging chamber, such that the first planar reflector is positioned at a bottom of the imaging chamber, and the second planar reflector is positioned proximate to a top corner of the imaging chamber. Furthermore, the first planar reflector is angled less than 45 degrees relative to a bottom surface of the imaging chamber. Adjustment means is coupled to the first planar reflector, the second planar reflector and the lens assembly for optimizing alignment between the first planar reflector, the second planar reflector and the lens assembly.

In a second aspect, the present invention provides an auto exposure measurement system for an X-ray digital image capturer. The X-ray digital image capturer emits light from an intensifying screen in response to received X-rays. The auto exposure measurement system includes a light sensor, a microprocessor and a digital imaging device. The light sensor receives the emitted light, and provides a signal corresponding to a level of received light. The microprocessor stores a predetermined image exposure parameter for receiving the signal and compares the level of received light to the predetermined image exposure parameter. The digital imaging device receives the emitted light, and is controllable by the microprocessor to generate digital image data when the level of the received light reaches the predetermined image exposure parameter.

In embodiments of the present aspect, the auto exposure measurement system further includes additional light sensors coupled to the microprocessor. Each light sensor can include a matched lens for receiving emitted light from specific areas of the intensifying screen, and the microprocessor can store a plurality of predetermined image exposure parameters, each corresponding to a desired image type.

According to a third aspect, the present invention provides an X-ray system for obtaining images of materials. The X-ray system includes a working surface, an X-ray emitter, a digital image capturer, a computer and a monitor. The working surface has one side for mounting the materials. The X-ray emitter is slidably mounted to the working surface for emitting X-rays towards an area of the working surface supporting the materials. The digital image capturer is connected to the X-ray emitter and positioned on an opposite side of the working surface. The digital image capturer provides digital image data corresponding to the X-rays passing through the materials. The computer receives and stores the digital image data. The computer provides a viewable image corresponding to the digital image data. The monitor displays the viewable image provided by the computer.

In an embodiment of the third aspect, the digital image capturer can include a light generator for receiving the X-rays and for emitting light in response to the received X-rays, a first planar reflector for reflecting the emitted light, a second planar reflector positioned for receiving the emitted light from the first planar reflector, and reflecting the emitted light, and a fast relay-optics system for receiving the emitted light from the second planar reflector and for focusing the emitted light onto a digital imaging device. The digital imaging device generates the digital image data.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Generally, the present invention provides a digital X-ray system for capturing high quality images by maximizing the collection of emitted light from an intensifying screen in response to X-ray impact. The digital X-ray system includes a housing having an intensifying screen for receiving emitted X-rays and a combination of two planar reflectors for optimizing the light path between the intensifying screen and the lens assembly. A CCD chip receives the light from the lens assembly, to provide a digital image for immediate on-board processing or post-processing by a computer. The housing is compact, and can be used as a direct replacement for traditional film cartridges without major modifications to the system. The lens assembly includes freeform matched lenses to remove any optical distortions, and the housing includes a light sensor for providing exposure measurement and feedback. The system is designed to be quasi-monochromatic to maintain consistent image quality over the entire area of the intensifying screen.

Figure 3:
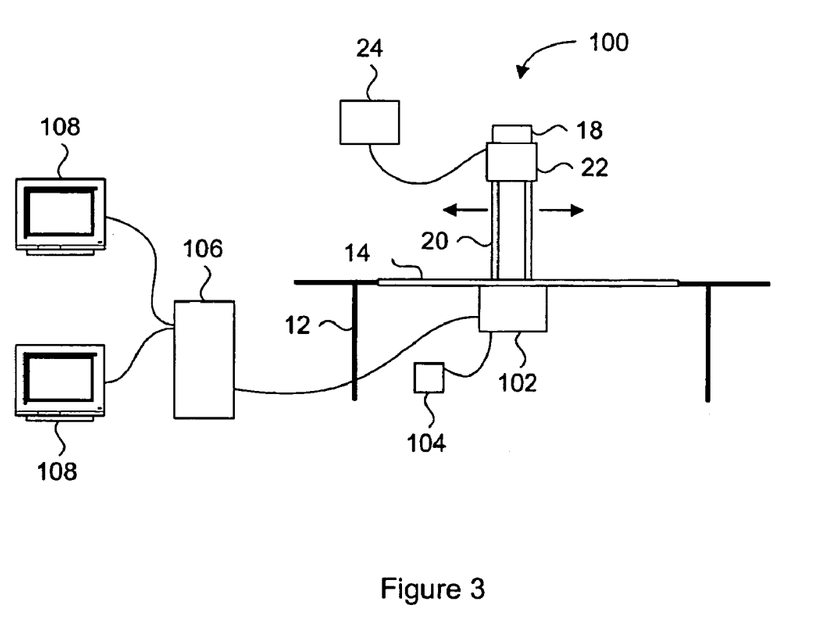
FIG. 3 is a block diagram of a digital X-ray imaging system according to an embodiment of the present invention.

A digital X-ray system according to an embodiment of the invention is shown in FIG. 3. This particular embodiment of the present invention is illustrated in the X-ray table application previously shown in FIG. 1. Table X-ray system 100 is similar to the system shown in FIG. 1, thus the same reference numerals refer to the same components that have been previously described for the system in FIG. 1. However, the film cartridge/cassette 16 of FIG. 1 is now replaced with the digital X-ray system according to an embodiment of the present invention. The digital X-ray system includes a digital image capturer 102 mounted underneath working surface 14, a power supply 104 for powering the digital image capturer 102, a computer 106 connected to the digital image capturer 102 via TCP/IP fast Ethernet connection, and monitors 108. The digital image capturer 102 is slidable along the working surface 14 with the X-ray emitter 18, and includes optical elements for concentrating light and a digital imaging device such as a CCD chip, for capturing the image. Also included within image capturer 102 is at least one light sensor for initiating image capture when the X-ray emitter 18 is turned on, and for providing user feedback regarding the effective dose. Further details of the digital image capturer 102 are discussed later with reference to FIG. 4.

Once an image is captured, the data is transferred to computer 106 for further processing and storage. From the computer 106, an operator can control various aspects and settings of the digital image capturer 102, and organize the images in a database to record patient number, image capture date and user notes that may be relevant to the image. The images have a dimension of 2048 rows by 3072 columns, and at 16-bit resolution, results in image sizes of about 12 megabytes. Thus, the computer 106 can include mass storage devices such as a CD-Writer or DVD-Writer for making digital copies of the images for archiving or transfer, and can be networked for direct transfer via email or FTP to other practitioners for evaluation. One monitor 108 can be located proximate to the operator for immediate viewing and analysis of the captured image, while another monitor 108 can be located in a different location for administrative and diagnostic purposes. In the present embodiment, one computer 106 is shown connected to one digital image capturer 102, however, multiple digital image capturers 102 can be controlled by the same computer 106 as each digital image capturer 102 can be separately addressable. Alternatively, multiple computers can be coupled to a single digital image capturer 102.

Of course, should hard copies of any image be required, a high quality printer can be coupled to computer 106 to print one or more copies of the image at any time. Those of skill in art will understand that once the image data is stored in computer 106, image processing algorithms can be executed to enhance the view-ability of the image. For example, the images can be processed with available commercial software packages to add color to traditional black and white images to highlight specific organic materials, such as muscle, bone and tendons.

Figure 4:
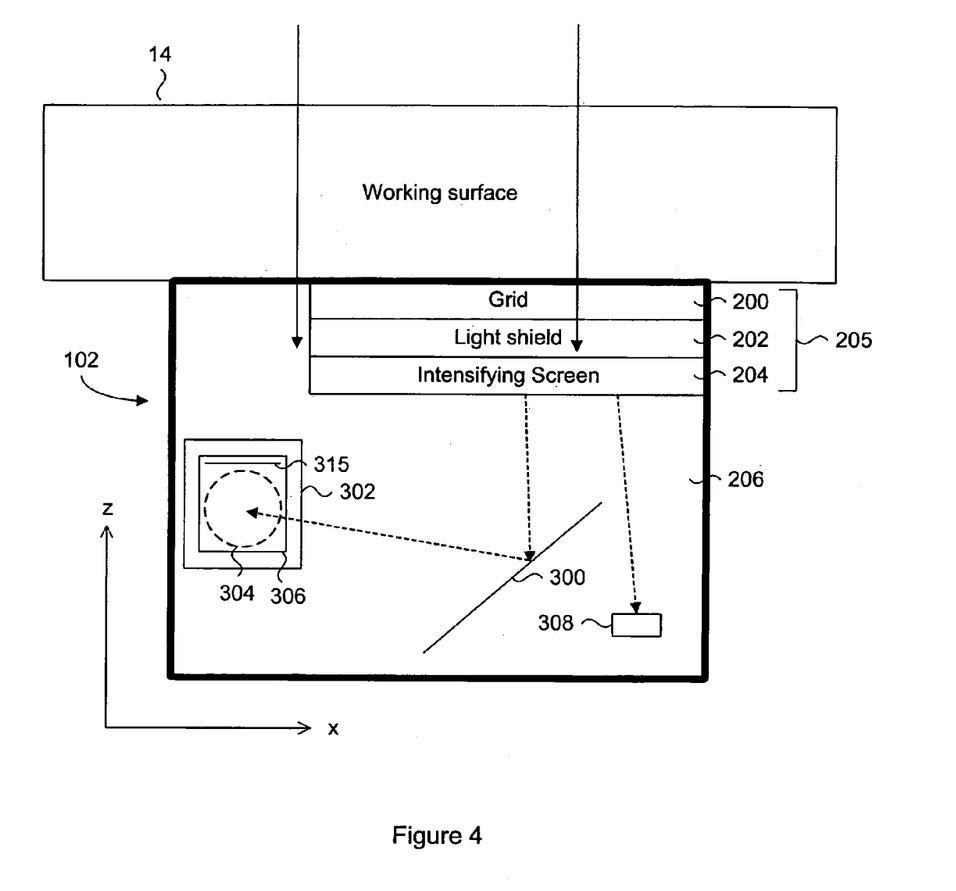
FIG. 4 is an illustration of a digital image capturer used in the X-ray imaging system of FIG. 3, according to an embodiment of the present invention.

A description of the components of digital image capturer 102 now follows with reference to FIG. 4. Digital image capturer 102 is mounted underneath working surface 14 and includes an X-ray grid 200, a light shield 202, an intensifying screen 204, and imaging chamber 206. Collectively, elements 200, 202 and 204 form a light generator 205. The dimensions of digital image capturer 102 are preferably constrained to a volume of 25×18×15 inches. X-ray grid 200 and intensifying screen 204 can be the same as X-ray grid 25 and intensifying screen 28 respectively of FIG. 2. Light shield 202 can be constructed of bakelite or carbon fiber, but can also be made of any material that is opaque to light. Bakelite and carbon fiber are preferred for their high transparency to X-rays. The purpose of light shield 202 is to block all external light from entering imaging chamber 206, as external light adds noise to the image, thus reducing image quality. Hence, imaging chamber 206 should receive only light emitted from intensifying screen 204.

Imaging chamber 206 is a rectangular volume having dimensions of about 18×23 inches by 15 inches. The chamber is sealed to prevent dirt and excessive humidity from entering the enclosure. Imaging chamber 206 is responsible for collecting and concentrating a maximum amount of emitted light from intensifying screen 204. In a preferred embodiment, imaging chamber 206 includes two planar reflectors 300 and 302, a lens assembly 304, and a CCD electronics board 306. The lens assembly 304, and CCD electronics board 306 are components of the fast relay-optics system, for ensuring that the image being imprinted upon the CCD chip is effectively free of distortions and other image degradations. Preferably, reflectors 300 and 302, and lens assembly 304 are positioned relative to each other such that the distance traveled by the light within imaging chamber 206 is maximized.

Imaging chamber 206 can include at least one light sensor 308. It is noted that the CCD electronics board 306 is located outside the volume delimited by the grid 200 and the bottom of imaging chamber 206. This is to ensure that the electronics are isolated from any X-rays that may pass into the imaging chamber 206. Lens assembly 304 also includes a lead coating on surface 315.

Figure 5:
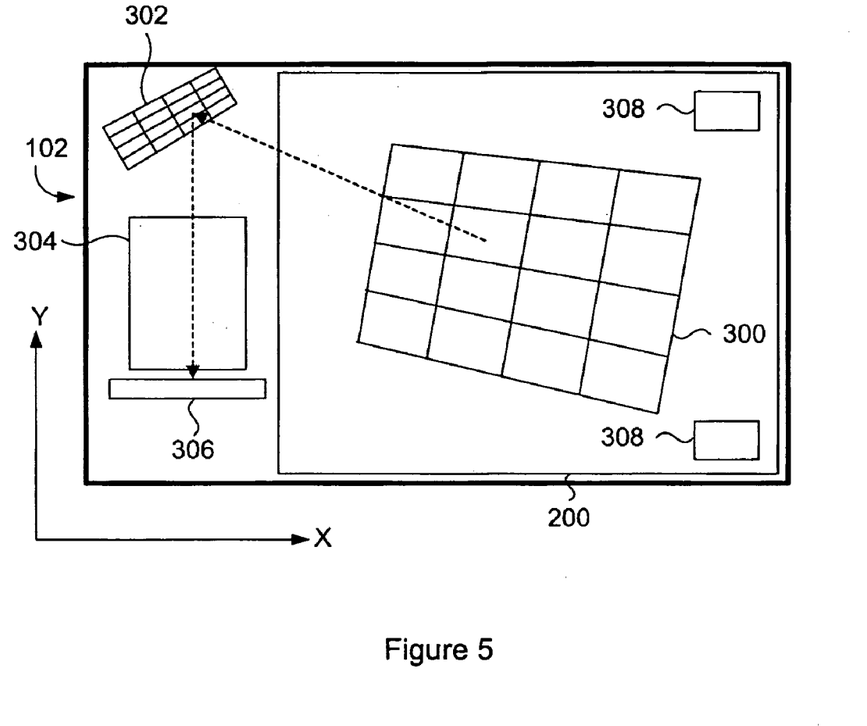
FIG. 5 is a top view of the digital image capturer of FIG. 4.

As shown in FIG. 4, light emitted from intensifying screen 204 is collected by a reflector 300 near the bottom of the imaging chamber 206, and reflected across and up to a second reflector 302 positioned near the top left of imaging chamber 206. The second reflector 302 then reflects the light into lens assembly 304, which then applies corrections to the light before receipt by the CCD device mounted upon CCD electronics board 306. FIG. 5 is a top view of the imaging chamber 206 of FIG. 4 to illustrate the x-y co-ordinate positioning of reflectors 300 and 302 relative to the imaging chamber 206.

As shown in the top view of FIG. 5, two light sensors 308 are placed on either side of reflector 300, and outside of the reflected light path. The angles of reflector 300 and reflector 302 are set such that lens assembly 304 and CCD electronics board 306 is oriented in the y axis. However the angles of reflector 300 and reflector 302 could be set such that lens assembly 304 and CCD electronics board 306 could be oriented in any direction in the y-z plane.

Reflector 300 is normally flat but could also be curved in shape. Reflector 302 is normally flat but could also be curved in shape. The purpose of the reflectors is to position the CCD at an optimal distance from the intensifying screen while preserving image quality. At an optimal distance, it is possible to increase collection of light with larger lenses. Since the optimal distance of the light path varies between 27 and 30 inches, the preferred embodiment uses a combination of two reflectors organized in a three-dimensional configuration to position the CCD at such a distance within the defined size of the imaging chamber of the preferred embodiment, as shown in FIG. 5. In order to effectively use the maximum distance of the light path available within the imaging chamber, reflector 300 plane is positioned at the bottom centre of the imaging chamber and redirects the light path to the top, left and back corner of the imaging chamber, where reflector 302 is located. Reflector 302 then redirects light path to the lens assembly located at the top left edge of the imaging chamber. The 3-D light path coupled with the use of two reflectors allows for the design of smaller imaging chamber dimensions. Both reflectors 300 and 302 are molded resin substrates or glass surfaces with an aluminum or equally reflective surface coating. In particular, by having reflector 302 disposed near the top of imaging chamber 206, reflector 300 can be arranged at an angle of less than 45 degrees relative to the bottom surface of imaging chamber 206. Thus, less space in the z-axis is occupied by reflector 300 and a reduction in the size of imaging chamber 206 can be realized. The previously discussed arrangement is one example of a 3D configuration, and other 3D configurations of the reflectors can be realized within the scope of the present invention. For example, lens assembly 304 and CCD electronics board 306 can be positioned at a bottom corner of the imaging chamber, and angled such that reflected light is received from appropriately angled reflector 302.

Those of skill will understand that control of image sharpness becomes more difficult as the working distance is further decreased. Therefore, due to the unique 3D configuration of reflectors 300 and 302, a longer light path is achievable within a smaller imaging chamber while preserving image quality and possible use of large lenses. Hence more light than prior art systems can be captured from the intensifying screen 204 and reflected onto the CCD chip via reflectors 300 and 302 and lens assembly 304.

Lens assembly 304 includes a series combination of lenses for correcting and focusing the light from reflector 302 onto an imaging device, such as a CCD chip. In a preferred embodiment, the lens assembly 304 includes nine plastic and glass lenses, where select lenses can be aspherical or spherical in shape. The designed lenses have the specific shapes that perfectly match the light path created by the reflector combination for the corrected field of view. To optimize quality and cost, the spherical lenses are preferably made of glass or plastic while the aspherical lenses are made of plastic. The sizes of the lens can be optimized to maximize light collection. Other designs may include as few as 5 lenses to as many as 15 lenses.

Generally, the lens assembly performs standard optical correction. In particular, the distortions in the light path caused by reflectors 300 and 302, are fully corrected by the lenses within lens assembly 304. Spherical, linear and chromatic distortions can be corrected with the appropriate corrective lenses. Moreover, the lenses within lens assembly 304 have an optimized shape for optical aberration correction, including on-axis and off-axis aberrations. Preferably, the lens assembly 304 is designed to best match the size of the intensifying screen 204 to that of the CCD chip on the electronics board 306. Although the CCD sensor array size may not perfectly match the size of the intensifying screen 204, adjustments to the lens assembly 304 can be made such that the image reduction ratio of the final image presented to the CCD chip matches the x and y dimensions of the CCD sensor array.

According to an embodiment of the present invention, the lens assembly 304 can be quasi-monochromatic, meaning that only specific wavelengths of light are received by the CCD chip. While prior art systems try to provide a maximum amount of light to the CCD chip, the quasi-monochromatic system actually restricts the amount of light to the CCD chip.

Figure 6:
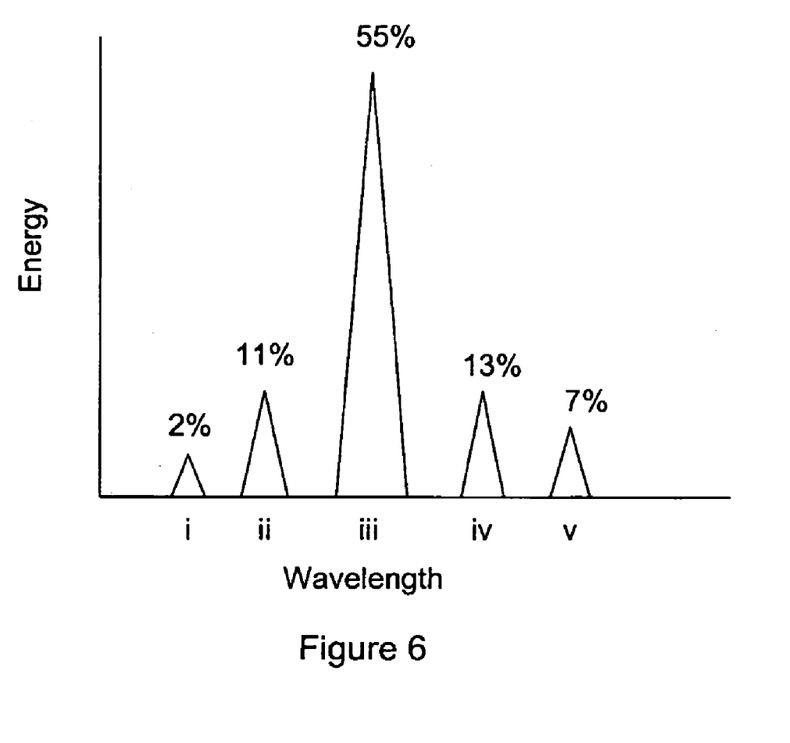
FIG. 6 is a spectral plot of light wavelengths versus energy.

FIG. 6 shows a wavelength spectrum demonstrating those wavelengths of light which are most relevant to digital X-ray image capture. Wavelengths i through v represent 88% of the light energy that is available, where i represents the 425 nm to 475 nm range, ii represents the 480 nm to 510 nm range, iii represents the 530 nm to 570 nm range, iv represents the 580 nm to 610 nm range, and v represents the 615 nm to 630 nm range. The contribution of wavelengths i, ii, iv and v are small, and eventually become dispersed over too many pixels at the intensifying screen edges. Accordingly, the image sharpness cannot be effectively controlled, and image degradation results. However, by restricting the light to wavelength iii, control of the image sharpness is facilitated across the entire area of the intensifying screen. For example, the image sharpness at the centre of the screen has been demonstrated to be less than 1 pixel wide, while the image sharpness at the edges of the screen has been demonstrated to be 1.25 pixels wide. Hence the spot size (measure of image sharpness) is consistently similar in size to a CCD pixel. Despite the reduced level of light received by the CCD chip, the consistent spot size across the entire area of the intensifying screen results in a sharper image across the entire image area.

To restrict the light to a single wavelength range, a 2-cavity bandpass filter coating can be applied to the surface of any lens of lens assembly 304. In the preferred embodiment, the bandpass filter is made of thin dielectric layers, using materials such as Silicon Dioxide ($SiO_2$) and Zirconium Dioxide ($ZrO_2$). The bandpass filter is transparent to wavelengths from 530 to 570 nanometers only, which includes photons of the main light peak of the intensifying screen, as shown in FIG. 6. Those of the other peaks will be filtered out by the bandpass filter. The main peak represents 55% of the total light energy emitted by the intensifying screen. As an alternative to the preferred embodiment, a bandpass filter of different materials, or with a different bandwidth, or with a different number of cavities, may be used.

The CCD electronics board 306 can include standard components required for basic functionality of the mounted CCD chip, but can further include additional processing circuits, such as microprocessor, specifically a digital signal processor (DSP), to execute image processing algorithms. Standard image processing algorithms can include noise suppression, flat fielding, dead pixel compensation and distortion correction, for example. Such standard imaging processing algorithms are well known in the digital imaging field, and may require calibration of the CCD chip to generate calibration data such as pixel gain coefficients for flat fielding calibration, pixel non-uniformity and vignetting compensation of the digital image data. Dark noise data can be used for thermal noise compensation of the digital image data, dead pixel mapping data can be used for dead pixel compensation of the digital image data, and distortion data can be used for distortion correction of the digital image data. While such data can be stored in the computer, the CCD electronics board 306 can include non-volatile memory such as Flash memory, for storing the data. Therefore, each digital image capturer 102 is pre-optimized during assembly, and executes the standard image processing algorithms transparently to the operator. The Flash can also store an error log of anomalies or problems reported by the DSP or microprocessor, for access during diagnostic checks.

Other components of the CCD electronics board 306 can include:

A fan to cool the electronics

A temperature control sensor to monitor the electronics temperature

A 16 bit A/D converter to translate the CCD pixel values into digital form

64 MB or RAM

A Fast Ethernet interface to allow message and image exchanges with the computer 106

An RS-232 serial port for configuration and debugging purposes

An NTSC/PAL video port for low resolution image display

A PhotoMOS relay (38 VDC, 2A) for testing

Control logic

Figure 7:
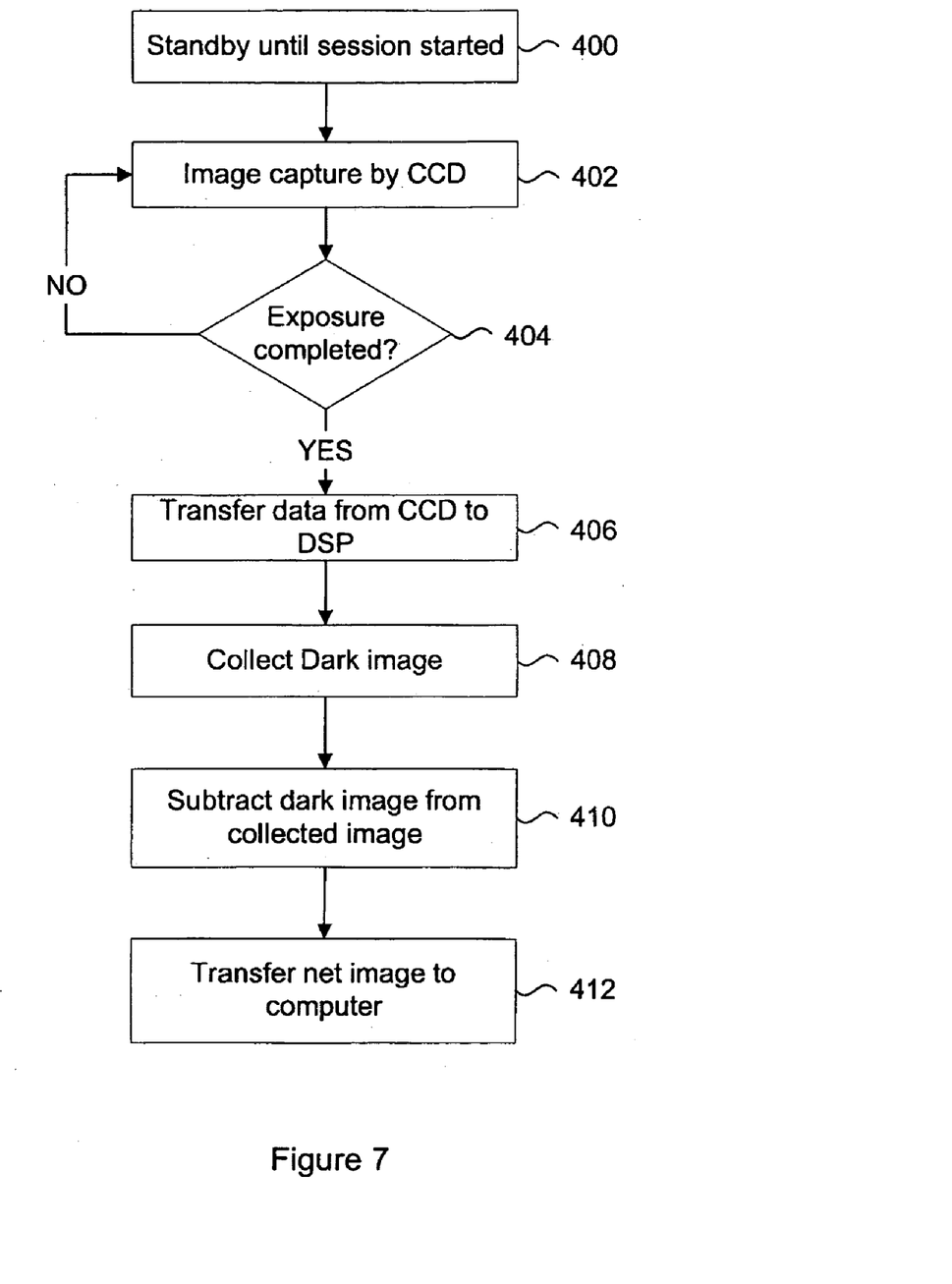
FIG. 7 is a flowchart showing an embodiment of a mehtod of the present invention.

According to a presently preferred embodiment, the method of FIG. 7 can be executed by the CCD electronics board 306 for capturing an image. At step 400, CCD electronics board 306 remains in standby mode, and no images are captured. At step 402, X-ray exposure has begun and the process for capturing the X-ray image begins. When the light sensors 308 detect light, the CCD chip begins charge accumulation. At step 404, a determination is made as to whether or not charge collection should terminate. This can be based on a configurable exposure time or on the X-ray exposure time duration. The method loops back to step 402 if the predetermined exposure time has not yet been reached and the light sensors are still detecting light. If the predetermined exposure time has been reached or the light sensors have stopped detecting light, then the image is transferred from the CCD to the DSP at step 406. Then at step 408, an optional dark image routine is executed, being a repeat of steps 402 to 406, but for the same exposure time, except that no X-rays are emitted. At step 410, the dark image is subtracted from the previously collected image, to provide a net pre-processed image, which is then transferred to the computer 106 at step 412. Once received by computer 106, the pre-processed image can then be subjected to a variety of post processing algorithms.

In addition to the standard image processing algorithms, specific image processing algorithms can be included. For example, the raw data image can be processed to visually highlight specific tissues that the operator desires to see. The image can be processed to improve viewability by adjusting sharpness, contrast and brightness. The image viewability can be augmented through colorization through well known techniques. Naturally, those of skill in the art will understand that there are many types of image processing techniques that can be applied to the digitally captured image. The DSP or microprocessor can be configured to receive feedback from the light sensors 308 in order to control/optimize the image capture process. For example, the signal from the light sensors 308 can determine the particular image processing algorithm to apply in order to optimize viewability of image. As will be discussed later, light sensors 308 can be used to initiate and end the image capture process.

While CCD electronics board 306 is coupled to the computer via a communications cable, an alternate means for communication can include wireless transmissions according to well known standards, such as Bluetooth and WiFi. Persons of skill in the art will understand that the CCD electronics board 306 would be designed to include the appropriate transceiver circuits to enable wireless communication to the computer. The CCD electronics board can include additional memory to provide temporary storage of images prior to transfer to the computer. Such memory is useful in applications where multiple images are captured during a session.

Although not shown in the figures, reflectors 300 and 302, lens assembly 304 and CCD electronics board 306 are mounted to a supporting frame fixed to the imaging chamber 206. While the supporting frame provides general alignment between the components, additional adjustment means can be incorporated to provide fine adjustment alignment. In alternate embodiments, the fine adjustment means can include manual adjustment components or X-ray tolerant electromechanical components that can be controlled to auto-adjust during maintenance checks. In an auto-adjusting embodiment, the adjustments can be calibrated to an intensity or positioning of light received by the sensor array of the CCD chip.

Light sensor 308 can be any commercially available device (photodiode, phototransistor, or other) installed within the imaging chamber and outside the path of light reflected by reflectors 300 and 302. Light sensor 308 is preferably connected to CCD electronics board 306, and specifically to a DSP or microprocessor for execution of algorithms in response to the signal received from light sensor 308. A basic application of light sensor 308 is automatic activation of the CCD chip to begin image capture. Another application is automatic exposure measurement by coupling light sensor 308 with a matched lens and arranged to collect light from specific areas of the intensifying screen 204. Unlike ionization chambers which intercept X-rays, the light sensor 308 does not interfere with either the X-rays or light received by reflector 300 to reduce light collection efficiency. For example, the light sensor and matched lens can be arranged to collect light only from the pulmonary areas of an appropriately positioned patient. By appropriately calibrating the light sensor 308, the microprocessor can automatically terminate image capture and provide notification to the operator to stop X-ray emission once a sufficient amount of light has been received. Then the image data can be generated and sent to the microprocessor for image processing.

More specifically, the microprocessor can be programmed to store predetermined image exposure parameters, such as light level thresholds, and to monitor the appropriate light sensors 308. The light sensors 308 provide a signal to the microprocessor, representing the received light level. When the received light level has reached the predetermined threshold, the microprocessor instructs the CCD chip to end image capture operations and send the image data. Accordingly, any number of light sensors 308 can be used in the imaging chamber 206.

Advanced operations can be realized with light sensor 308. One such operation is multiple image capture from a single session. In particular, since different tissue types are better imaged at specific X-ray doses, a patient can be subjected to a predetermined dose while several images can be captured at different times during the session. For example, the CCD chip can be controlled to capture an image when predetermined thresholds of light have been reached. Each predetermined threshold can be calibrated to correspond to a particular dose effective for highlighting a specific tissue. Therefore in a single session, multiple images highlighting specific tissues can be obtained. In contrast to film based systems, the patient must be subjected to multiple sessions in order to obtain the different images.

Another advanced operation is to provide feedback to the operator or system regarding the dose, and to calculate amounts by which the dose should be adjusted by in order to obtain the optimal image. For example, calibration data relating to light intensities corresponding to specific doses can be collected and stored in the microprocessor memory in the factory. During operation, a dose is administered and the light sensor 308 can provide feedback to the microprocessor for calculating an appropriate dose adjustment in order to obtain an optimal image. Those of skill in the art should understand how to extrapolate or interpolate the dose adjustment level through simple calculations or modeling algorithms executed by the microprocessor. The optimal image can depend on the tissue type of interest, brightness levels, and/or contrast levels. Of course, the thresholds for comparing the session dose against can be pre-programmed in the microprocessor.

Any suitable method for fixing the light sensor(s) 308 and corresponding matched lenses to the imaging chamber 206 can be used. For example, multiple light sensors 308 can be mounted to a rigid board, and a plastic sheet with integrated matched lenses aligned with each corresponding light sensor 308 can be overlaid on top of the board. The components are inexpensive to purchase, fabricate and assemble.

In summary, the previously described components cooperate together to generate high quality digital images in a compact assembly. The 3D configuration of reflectors 300 and 302 maximizes the light path length, which allows for flexible arrangement of reflectors 300 and 302, and the use of larger lenses within lens assembly 304. As previously discussed, the lenses within lens assembly 304 have an optimized shape for optical aberration correction, including on-axis and off-axis aberrations. The lens assembly restricts the applied light to a specific wavelength range and applies optical correction to provide sharper images, and automatic exposure measurement feedback via one or more light sensors improves efficiency by automating the image capture process.

Therefore, the digital image capturer 102 according to the embodiment of the present invention can obtain digital images having a quality equal or superior to prior digital X-ray systems at much lower costs. Due to its relatively compact size, the digital image capturer 102 can be easily used as a retro-fit for existing film-based X-ray machines, saving the clinic or hospital from costly replacement of the system. Furthermore, since most clinics employ computers to store patient information in databases, no additional computer is required, since the existing computer can be installed with the appropriate applications and software for communicating with the digital image capturer 102. As previously mentioned, image processing algorithms can be integrated with the installed software, and updated as required. Furthermore, the computer can include software to perform diagnostic checks upon the system.

While the present embodiments have been described using a CCD imaging chip, alternate digital imaging devices can be used with equal effectiveness, such as CMOS image sensors for example.

The presently described embodiments can be applied to other applications with the appropriate modifications that should be known to those of skill in the art. These applications can include microelectronics inspection, composite material evaluation, weld and casting inspection, aeronautics and space products examination, parcel inspection for content validation (when insuring parcel transit), parcel inspection for security purposes, luggage inspection at airports and food inspection, for example.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A digital image capturer for receiving X-rays and providing digital image data corresponding to the received X-rays, the digital image capturer comprising:
   a light generator for receiving the X-rays and for emitting light in response to the received X-rays;
   a first planar reflector for reflecting the emitted light, an orientation of the first planar reflector defined by a first vector, the first vector normal to the first planar reflector,
   a second planar reflector positioned for receiving the emitted light from the first planar reflector, and reflecting the emitted light, an orientation of the second planar reflector defined by a second vector, the second vector normal to the second planar reflector, the first vector and the second vector lying in different planes; and,
   a fast relay-optics system for receiving the emitted light from the second planar reflector and for focusing the emitted light onto a digital imaging device, the digital imaging device generating the digital image data.

2. The digital image capturer of claim 1, wherein the light generator includes:
   a light shield positioned for receiving the X-rays and for blocking external light; and
   an intensifying screen adjacent to the light shield for emitting light in response to the X-rays passing through the light shield.

3. The digital image capturer of claim 2, wherein the light generator further comprises an X-ray grid mounted to the light shield.

4. The digital image capturer of claim 2, wherein the light shield is constructed from a material opaque to light and transparent to X-rays.

5. The digital image capturer of claim 4, wherein the material is selected from the group consisting of bakelite and carbon fiber.

6. The digital image capturer of claim 1, wherein the fast relay-optics system comprises:
   a CCD electronics board having the digital imaging device, and
   a lens assembly positioned for receiving the emitted light from the second planar reflector, the lens focusing the emitted light onto the digital imaging device.

7. The digital image capturer of claim 6, wherein the lens assembly comprises a combination of spherical and aspherical lenses.

8. The digital image capturer of claim 6, wherein the lens assembly is quasi-monochromatic.

9. The digital image capturer of claim 8, wherein the lens assembly restricts light having wavelengths less than about 530 nm and greater than about 570 nm.

10. The digital image capturer of claim 8, wherein one of the lenses in the lens assembly is coated with a 2-cavity bandpass filter made of $SiO_2$ and $ZrO_2$.

11. The digital image capturer of claim 1, further comprising at least one light sensor coupled to the digital imaging device.

12. The digital image capturer of claim 11, wherein the at least one light sensor comprises a matched lens for receiving emitted light from a specific area of the intensifying screen.

13. The digital image capturer of claim 1, wherein the first planar reflector and the second planar reflector are housed in an imaging chamber.

14. The digital image capturer of claim 13, wherein the first planar reflector is positioned at a bottom of the imaging chamber, and the second planar reflector is positioned proximate to a top corner of the imaging chamber.

15. The digital image capturer of claim 13, wherein the first planar reflector is angled less than 45 degrees relative to a bottom surface of the imaging chamber.

16. The digital image capturer of claim 6, further comprising adjustment means coupled to the first planar reflector, the second planar reflector and the lens assembly for optimizing alignment between the first planar reflector, the second planar reflector and the lens assembly.

17. The digital image capturer of claim 6, wherein the digital imaging device comprises one of a CCD chip or a CMOS sensor.

18. The digital image capturer of claim 6, wherein the CCD electronics board comprises a microprocessor for receiving digital image data from the digital imaging device and for executing image processing algorithms upon the digital image data.

19. The digital image capturer of claim 6, wherein the CCD electronics board comprises non-volatile memory for storing imaging device calibration data.

20. The digital image capturer of claim 19, wherein the calibration data comprises at least one of pixel gain coefficients, pixel dark noise data, dead pixel mapping data and distortion data.

21. The digital image capturer of claim 18, wherein the microprocessor comprises a digital signal processor.

22. The digital image capturer of claim 1, wherein the fast relay-optics system includes an entrance port for receiving the emitted light from the second planar reflector, the entrance port facing a direction substantially orthogonal to a propagation direction of the X-rays.

23. An X-ray system for obtaining images of materials comprising:
   a working surface having one side for mounting the materials;
   an X-ray emitter slidably mounted to the working surface for emitting X-ray towards an area of the working surface supporting the materials;
   a digital image capturer connected to the X-ray and positioned on an opposite side of the working surface, the digital image capturer emitter sliding in unison with the X-ray emitter and providing digital image data corresponding to the X-rays passing through the materials, the digital image capturer comprising:
      a light generator for receiving the X-rays and for emitting light in response to the received X-rays:
      a first planar reflector for reflecting the emitted light, an orientation of the first planar reflector defined by a first vector, the first vector normal to the first planar reflector;
      a second planar reflector positioned for receiving the emitted light from the first planar reflector, and reflecting the emitted light, an orientation of the second planar reflector defined by a second vector, the second vector normal to the second planar reflector, the first vector and the second vector lying in different planes; and
      a fast relay-optics system for receiving the emitted light from the second planar reflector and for focusing the emitted light onto a digital imaging device, the digital imaging device generating the digital image data;
   a computer for receiving and storing the digital image data, the computer providing a viewable image corresponding to the digital image data; and
   a monitor for displaying the viewable image.

* * * * *